US00PP28569P2

(12) United States Plant Patent
Danziger

(10) Patent No.: US PP28,569 P2
(45) Date of Patent: Oct. 24, 2017

(54) ***CALIBRACHOA* PLANT NAMED 'DANOASUNLT'**

(50) Latin Name: *Calibrachoa hybrida*
Varietal Denomination: DANOASUNLT

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 0 days.

(21) Appl. No.: 14/999,065

(22) Filed: Mar. 25, 2016

(51) Int. Cl.
*A01H 5/02* (2006.01)

(52) U.S. Cl.
USPC ..... Plt./413

(58) Field of Classification Search
USPC ..... Plt./413
CPC ..... A01H 5/02
See application file for complete search history.

(56) References Cited

PUBLICATIONS http://www.nova.co.at/marsNova/en/instance/picture/Calibrachoa-Noa--Sunlight.xhtml?oid=9529932; Feb. 23, 2016; 2 pages.*

* cited by examiner

*Primary Examiner* — Kent L Bell
(74) *Attorney, Agent, or Firm* — Cassandra Bright

(57) ABSTRACT

A new and distinct *Calibrachoa* cultivar named 'DANOASUNLT' is disclosed, characterized by a semi-trailing compact habit, branching and an abundance of large, intensely yellow flowers. The new variety is a *Calibrachoa*, normally produced as an outdoor garden or container plant.

2 Drawing Sheets

Figure 1:
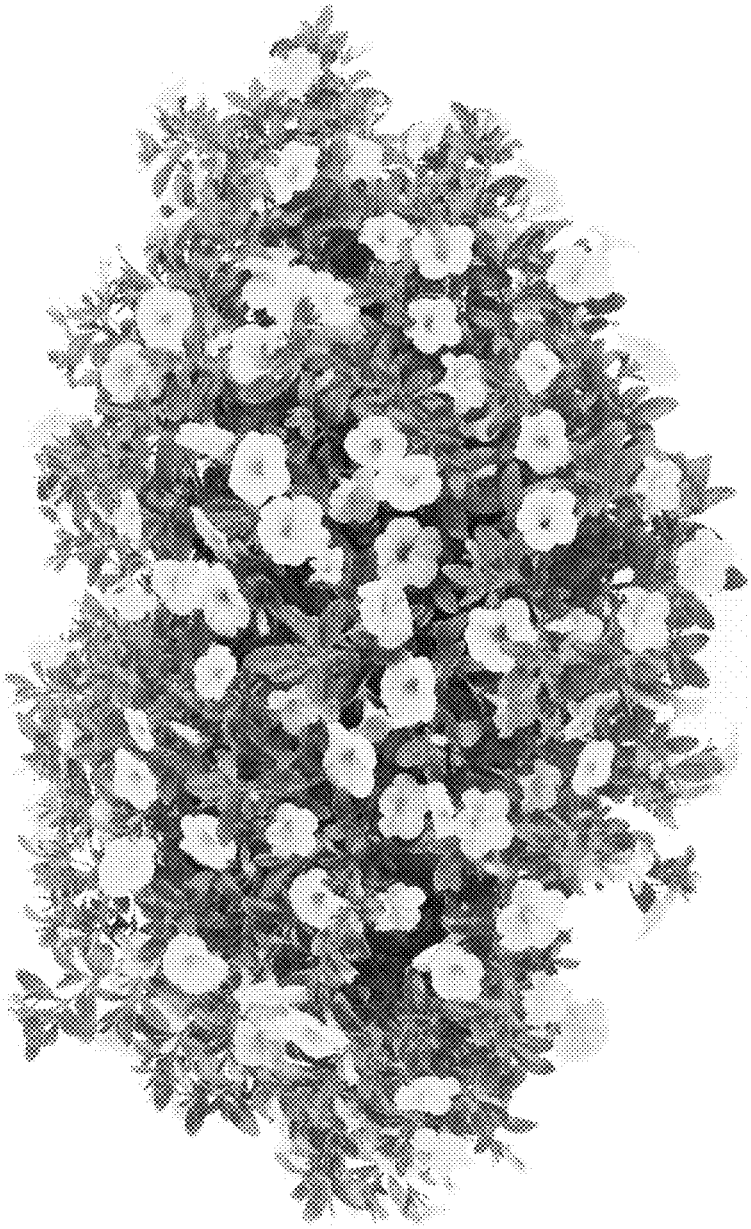

Latin name of the genus and species: *Calibrachoa hybrida.*

Variety denomination: 'DANOASUNLT'.

BACKGROUND OF THE INVENTION

The new *Calibrachoa* cultivar is a product of a planned breeding program conducted by the inventor, Gavriel Danziger in Moshav Mishmar Hashiva, Israel. The objective of the breeding program was to produce new *Calibrachoa* varieties. The cross resulting in this new variety was made during February of 2012.

The seed parent is the unpatented, propriety variety referred to as *Calibrachoa* 'cv. 11-2610'. The pollen parent is the, unpatented, propriety variety referred to as *Calibrachoa* 'cv. 11-2631'. The new variety was discovered in October of 2012 by the inventor in a group of seedlings resulting from the 2012 crossing, in a greenhouse in Moshav Mishmar Hashiva, Israel.

Asexual reproduction of the new cultivar 'DANOASUNLT' was first performed by terminal vegetative cuttings during October of 2012, at a greenhouse in Moshav Mishmar Hashiva, Israel. Subsequent propagation by vegetative cuttings has shown that the unique features of this cultivar are stable and reproduced true to type in more than 20 successive generations.

SUMMARY OF THE INVENTION

The cultivar 'DANOASUNLT' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DANOASUNLT' These characteristics in combination distinguish 'DANOASUNLT' as a new and distinct *Calibrachoa* cultivar:

1. Semi-trailing growth habit.
2. Moderately well branched growth.
3. Flower color is an intense yellow.
4. Large flower size.
5. Abundant flowering.

PARENT COMPARISON

Plants of the new cultivar 'DANOASUNLT' are similar to plants of the seed parent, *Calibrachoa* 'cv. 11-2610' most horticultural characteristics, however, plants of the new cultivar 'DANOASUNLT' differ in the following;

1. Semi-trailing growth habit, whereas the seed parent has a trailing growth habit.
2. Less branches than the seed parent.
3. Flower color is more intense yellow than the seed parent.
4. Smaller flowers than the seed parent.
5. More flowers per plant than the seed parent.

Plants of the new cultivar 'DANOASUNLT' are similar to plants of the pollen parent, *Calibrachoa* 'cv. 11-2631' most horticultural characteristics, however, plants of the new cultivar 'DANOASUNLT' differ in the following;

1. Semi-trailing growth habit, whereas the pollen parent has a mounded growth habit.
2. More branches than the pollen parent.
3. Flower color is an intense yellow, whereas the seed parent has light yellow flowers.
4. Larger flowers than the seed parent.
5. More flowers than the seed parent.

COMMERCIAL COMPARISON

Plants of the new cultivar 'DANOASUNLT' can be compared to the unpatented commercial variety *Calibrachoa* 'NOA Banana'. These varieties are similar in most horticultural characteristics; however, 'DANOASUNLT' differs in the following:

1. Growth habit of comparison variety is mounded, while the new variety has a semi-trailing growth habit.
2. Flower color of comparison variety is light yellow, while flower color of the new variety is an intense yellow.
4. Flowering time of the comparison variety is earlier than that of the new variety.
5. The comparison variety is very well branched, while the new variety is moderately branched.

Plants of the new cultivar 'DANOASUNLT' can also be compared to the patented commercial variety *Calibrachoa* 'DANOA37' U.S. Plant Pat. No. 19,958. These varieties are similar in most horticultural characteristics; however, 'DANOASUNLT' differs in the following:

1. Growth habit of comparison variety is mounded, while the new variety has a semi-trailing growth habit.
2. The comparison variety is less well branched than the new variety.
3. Flower color of comparison variety is yellow, while flower color of the new variety is an intense yellow.
4. Plant vigor of the comparison variety is weaker than the vigor of the new variety.
5. Flower size of the comparison variety is smaller than the flower size of the new variety.

BRIEF DESCRIPTION OF THE PHOTOGRAPHS

The accompanying photograph in FIG. 1 illustrates in full color a typical plant of 'DANOASUNLT' grown in a 13 cm pot in a greenhouse in Moshav Mishmar Hashiva, Israel.

Figure 2:
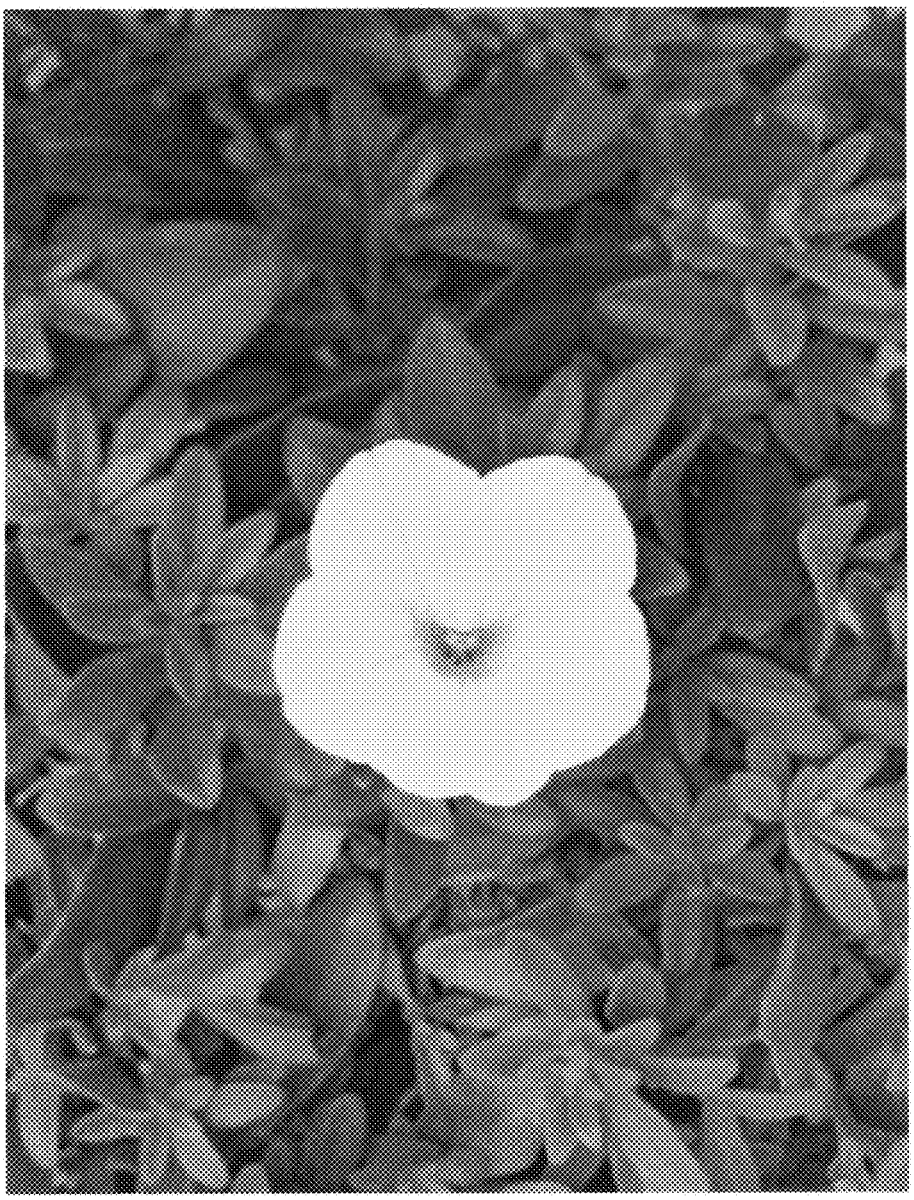

FIG. 2 illustrates in full color a typical flower of 'DANOASUNLT'. Age of the plant photographed is approximately 60 days from a rooted cutting in a 13 cm pot.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DANOASUNLT' plants grown in a greenhouse in Moshav Mishmar Hashiva, Israel, under natural lighting. Measurements were taken during April of 2015. The plants were approximately 60 days from a rooted cutting in a 13 cm pot. The growing temperature ranged from 18° C. to 35° C. during the days, 15° C. to 25° C. during the nights. Measurements and numerical values represent averages of typical plant types.

Botanical classification: *Calibrachoa hybrida* 'DANOASUNLT'.

PROPAGATION

Time to initiate roots: 10-14 days at approximately 20-22° C.

PLANT

Growth habit: Semi-trailing.
Height:
*To top of flowers.*—About 11 cm.
Plant spread: About 45 cm.
Growth rate: Medium.
Branching characteristics: Moderately branched.
Length of primary lateral branches: About 20 cm.
Diameter of lateral branches: About 0.2 cm.
Quantity of primary lateral branches: 8.
Characteristics of primary lateral branches:
*Form.*—Cylindrical.
*Diameter.*—About 0.2 cm.
*Color.*—RHS Green 137D.
*Texture.*—Slightly pubescent.
*Strength.*—Strong.
Internode length: About 1 cm.
Root description: Fibrous.

FOLIAGE

Leaf:
*Arrangement.*—Alternate.
*Quantity.*—Approximately 60 per branch.
*Average length.*—About 3 cm.
*Average width.*—About 1 cm.
*Shape of blade.*—Elliptic.
*Apex.*—Rounded.
*Base.*—Acute.
*Margin.*—Entire.
*Texture of top surface.*—Velvety.
*Texture of bottom surface.*—Velvety.
*Pubescence.*—Pubescent.
*Color.*—Young foliage upper side: RHS Yellow-Green 146 A. Young foliage under side: RHS Yellow-Green 146 B. Mature foliage upper side: RHS Yellow-Green 147 A. Mature foliage under side: RHS Yellow-Green 147 B.
*Venation.*—Type: Pinnate. Venation color upper side: RHS Yellow-Green 147 A. Venation color under side: RHS Yellow-Green 147 C.
*Petiole.*—Length: about 0.3 cm. Diameter: about 0.2 cm. Color: RHS Yellow-Green 147 A. Texture: Velvety.

FLOWER

Natural flowering season: Spring, Summer and Autumn, under natural Israeli conditions.
Days to flowering from rooted cutting: About 40 days.
Inflorescence and flower type and habit: Axillary, single flower, salverform shape. Flowers facing up and out.
Rate of flower opening: 3 to 4 days from bud to fully opened flower.
Flower longevity on plant: 4-7 days.
Approximate quantity of flowers per plant: About 80.
Persistent or self-cleaning: Self-cleaning.
Bud:
*Shape.*—Tubular.
*Length.*—About 2.5 cm.
*Diameter.*—About 0.7 cm.
*Color.*—RHS Yellow 6B.
Flower size:
*Diameter.*—About 3.2 cm.
*Length.*—About 2.5 cm.

*Flower tube diameter at distal end.*—About 1.0 cm.
*Flower tube diameter at proximal end.*—About 0.3 cm.

Petals:
*Length from throat.*—About 1.3 cm.
*Width.*—About 1.5 cm.
*Quantity.*—5.
*Texture.*—Velvety.
*Apex.*—Rounded.
*Base.*—Fused.
*Margin.*—Entire.

Color:
*When opening.*—Upper surface: RHS Yellow-Orange 14 A. Lower surface: RHS Yellow-Orange 14 B.
*Fully opened.*—Upper surface: RHS Yellow 12 A. Lower surface: RHS Yellow 12 B.
*Flower throat (inside).*—RHS Yellow 12 A.
*Flower throat, vein.*—RHS Yellow-green N144 A.
*Flower tube (outside).*—RHS Yellow 12 B.
*Flower tube, vein.*—RHS Yellow-green N144 B.
*Petal color, fading to.*—RHS Yellow 12 B.

Calyx/sepals:
*Quantity per flower.*—5.
*Shape.*—Linear.
*Length.*—About 1.5 cm.
*Width.*—About 0.4 cm.
*Apex.*—Rounded.
*Base.*—Fused.
*Margin.*—Entire.
*Texture.*—Velvety.
*Color.*—Upper Surface: RHS Yellow-Green 146 A. Lower surface: RHS Yellow-Green 146 B.

Peduncle: Not relevant.

Pedicel:
*Length.*—About 2 cm.
*Diameter.*—About 0.1 cm.
*Color.*—RHS Yellow-Green 146 C.
*Orientation.*—45 degrees.

Fragrance: None.

REPRODUCTIVE ORGANS

Stamens:
*Number.*—5.
*Filament length.*—About 1 cm.

Anthers:
*Length.*—About 0.1 cm.
*Shape.*—Rounded.
*Color.*—RHS Yellow 8 B.
*Pollen.*—Color: RHS Yellow 7 C. Quantity: moderate amount.

Pistil:
*Number.*—1.
*Length.*—About 1.2 cm.
*Style.*—Length: about 0.8 cm. Color: RHS Yellow-Green 145 A.
*Stigma.*—Shape: Rounded. Color: RHS Yellow-Green N144 B. Ovary Color: RHS Yellow-Green 145A.

OTHER CHARACTERISTICS

Seeds and fruits: About 30 brown, rounded seeds of about 0.5 mm diameter, per one brown, conical capsule.

Disease/pest resistance: Typical to other *Calibrachoa* varieties.

Temperature tolerance: 5-30° C.

Disease/pest resistance: Typical to known *Calibrachoa* varieties. Neither resistance nor susceptibility to the normal diseases and pests of *Calibrachoa* have been observed. Pests common to *Calibrachoa* include Aphids and thrips. Typical diseases are *Botrytis* and *Pythium.*

Temperature tolerance: 5° C. to 30° C.

Drought tolerance: No tolerance for drought.

What is claimed is:

1. A new and distinct cultivar of *Calibrachoa* plant named 'DANOASUNLT' as herein illustrated and described.

* * * * *